(12) United States Patent
Fujimoto et al.

(10) Patent No.: US 12,013,331 B2
(45) Date of Patent: Jun. 18, 2024

(54) DETERIORATION PREDICTION METHOD

(71) Applicant: NIPPON TELEGRAPH AND TELEPHONE CORPORATION, Tokyo (JP)

(72) Inventors: Norihiro Fujimoto, Musashino (JP); Hisatoshi Kasahara, Musashino (JP); Yosuke Okamura, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 543 days.

(21) Appl. No.: 17/417,374

(22) PCT Filed: Dec. 16, 2019

(86) PCT No.: PCT/JP2019/049230
§ 371 (c)(1),
(2) Date: Feb. 1, 2022

(87) PCT Pub. No.: WO2020/137666
PCT Pub. Date: Jul. 2, 2020

(65) Prior Publication Data
US 2022/0163441 A1 May 26, 2022

(30) Foreign Application Priority Data

Dec. 27, 2018 (JP) ................. 2018-246208

(51) Int. Cl.
*G01N 17/00* (2006.01)
*G01N 33/2045* (2019.01)
*G01N 33/38* (2006.01)

(52) U.S. Cl.
CPC ......... *G01N 17/006* (2013.01); *G01N 17/002* (2013.01); *G01N 33/2045* (2019.01); *G01N 33/383* (2013.01)

(58) Field of Classification Search
CPC .................................................. G01N 17/006
(Continued)

(56) References Cited

FOREIGN PATENT DOCUMENTS

CN 107870147 A * 4/2018 ........... G01N 17/006

OTHER PUBLICATIONS

Lan et al. Translation of CN 107870147 A. Published Apr. 2018. Accessed Feb. 2024. (Year: 2018).*

(Continued)

*Primary Examiner* — Walter L Lindsay, Jr.
*Assistant Examiner* — Philip T Fadul
(74) *Attorney, Agent, or Firm* — XSENSUS LLP

(57) ABSTRACT

A degradation predicting method is a degradation predicting method for predicting degradation of a reinforced concrete structure buried in the ground, the method including: a condensation occurrence condition evaluating step (S1) of evaluating a condensation occurrence condition on which condensation occurs on reinforcing steel; a condensation time calculating step (S2) of calculating a condensation time that is a total time in which condensation occurs on the reinforcing steel based on the condensation occurrence condition for each of a plurality of the reinforced concrete structures; a threshold determining step (S3) of determining a threshold of underground depth at which the reinforced concrete structure is less prone to degradation based on a relationship between the condensation time and a underground depth of the reinforced concrete structure; and a degradation predicting step (S4) of predicting degradation of a prediction-target reinforced concrete structure based on the threshold.

4 Claims, 9 Drawing Sheets

(58) Field of Classification Search
USPC .................................................... 73/118.01
See application file for complete search history.

(56) References Cited

OTHER PUBLICATIONS

Hirofumi Sugawara et al., Errors in Calculation of Satulation Vapor Pressure, Journal of Japan Society of Hydrology and Water Resources, 1994, pp. 440-443, vol. 7, No. 1.
Norihiro Fujimoto et al., Condensation generation mechanism in communication manholes, Japan Society of Civil Engineers 73rd Annual Academic Lecture, Aug. 2018, pp. 789-790.
Norihiro Fujimoto et al., Weak points of communication manholes and their deterioration mechanism, IEICE Technical Report, 2018, pp. 51-56, vol. 117, No. 387.

* cited by examiner

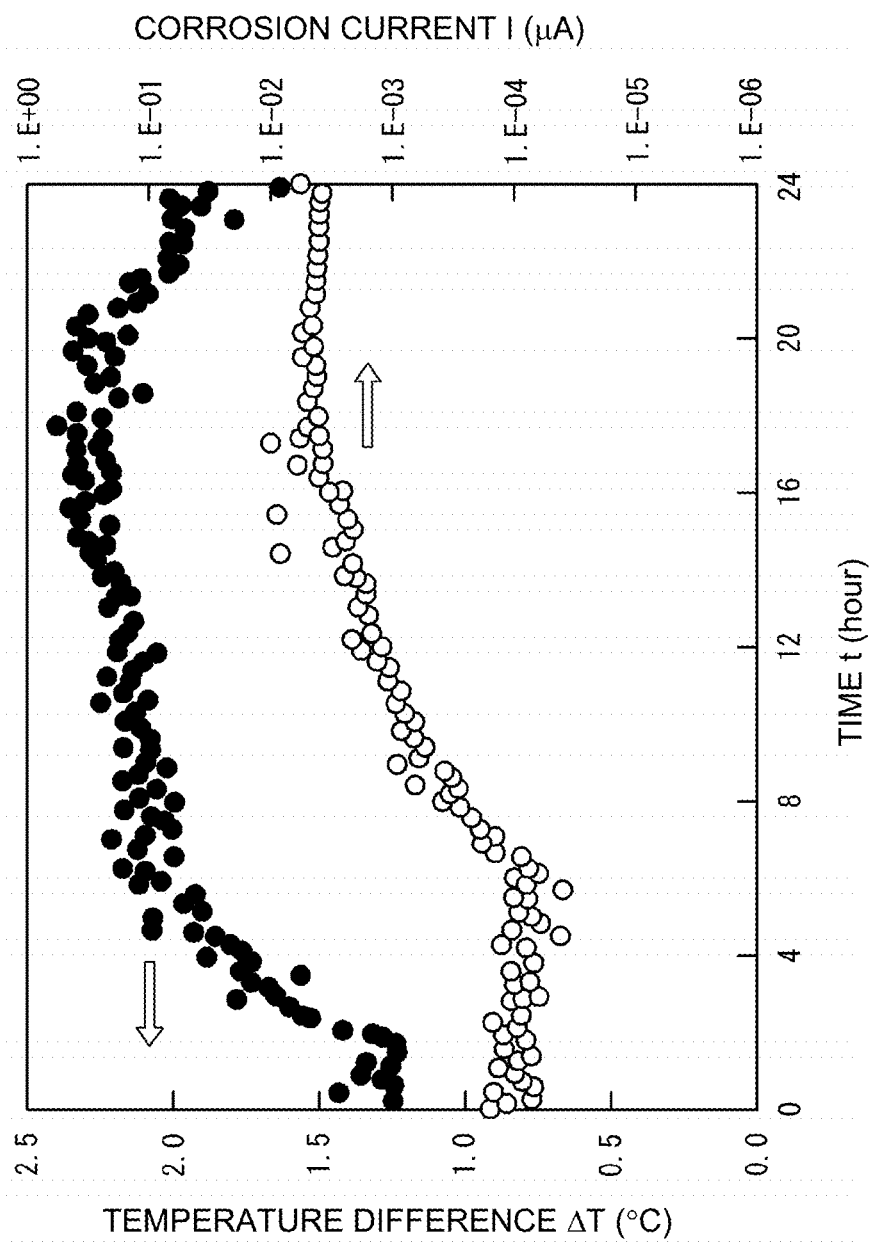

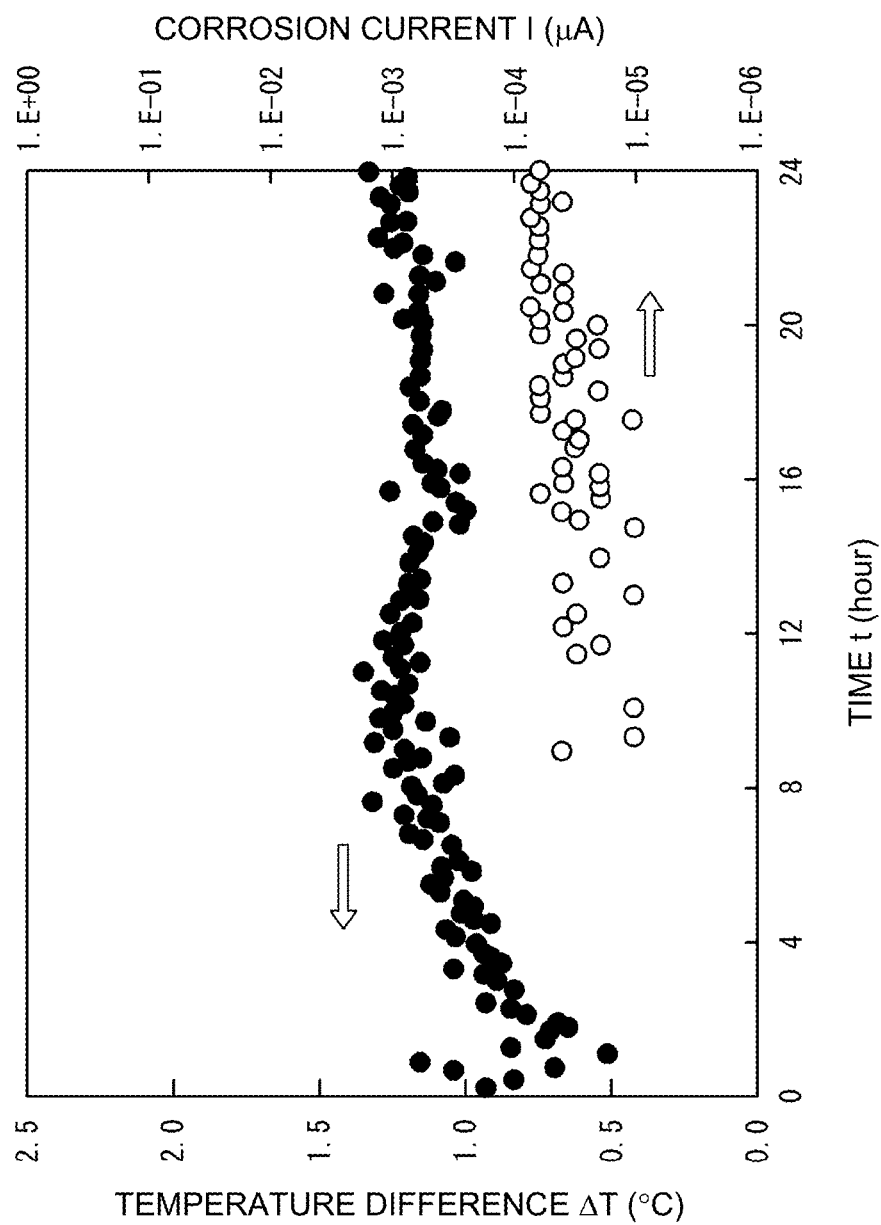

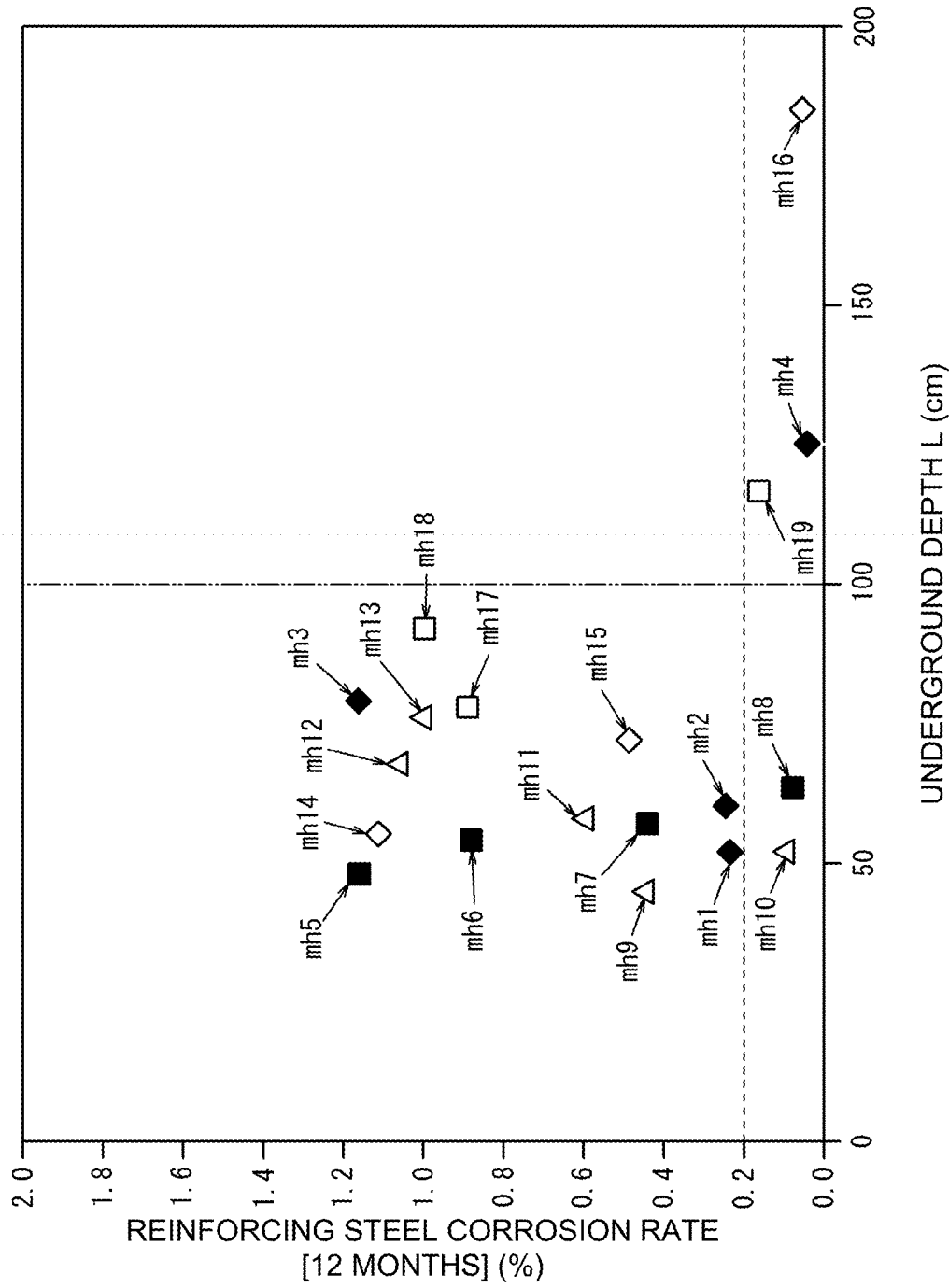

DETERIORATION PREDICTION METHOD

TECHNICAL FIELD

The present invention relates to a degradation predicting method.

BACKGROUND ART

It is conventionally known that reinforced concrete structures, which are made of a combination of reinforcing steel and concrete, degrade such as due to carbonation of the concrete caused by carbon dioxide in the atmosphere, volume expansion of the reinforcing steel caused by rusting, cracking of the concrete due to increase in the internal pressure, and corrosion of the reinforcing steel caused by condensation. In particular, it is known that there is a tendency that reinforced concrete structures buried in the ground are more prone to experience the occurrence of condensation on the reinforcing steel and hence more prone to degradation as their underground depth is smaller.

CITATION LIST

Non-Patent Literature

Non-Patent Literature 1: Norihiro Fujimoto, Hisatoshi Kasahara, Tomoyasu Nagai, 2018 Japan Society of Civil Engineers Annual Meeting, V-395 Mechanism of Condensation Occurrence in Communication Manholes Non-Patent Literature 2: Norihiro Fujimoto, Hisatoshi Kasahara, Tomoyasu Nagai, IEICE Technical Report, vol. 117, no. 387, OFT2017-67, pp. 51-56, January 2018

Non-Patent Literature 3: Hirofumi Sugawara, Junsei Kondo, Journal of Japan Society of Hydrology & Water Resources 7(1), pp. 440-443 (1994)

SUMMARY OF THE INVENTION

Technical Problem

However, in conventional studies, there has been difficulty in quantitatively determining a threshold of underground depth at which reinforced concrete structures buried in the ground are less prone to degradation. For that reason, there has been a problem of insufficient accuracy of predicting degradation of a prediction-target reinforced concrete structure.

It is an object of the present invention, which has been made in view of the above circumstances, to provide a degradation predicting method that can accurately predict degradation of a reinforced concrete structure buried in the ground.

Means for Solving the Problem

To solve the above problem, a degradation predicting method according to the present invention is a degradation predicting method for predicting degradation of a reinforced concrete structure buried in the ground, the method characterized by including: a condensation occurrence condition evaluating step of evaluating a condensation occurrence condition on which condensation occurs on reinforcing steel; a condensation time calculating step of calculating a condensation time that is a total time in which condensation occurs on the reinforcing steel based on the condensation occurrence condition for each of a plurality of the reinforced concrete structures; a threshold determining step of determining a threshold of underground depth at which the reinforced concrete structure is less prone to degradation based on a relationship between the condensation time and a underground depth of the reinforced concrete structure; and a degradation predicting step of predicting degradation of a prediction-target reinforced concrete structure based on the threshold.

Effects of the Invention

According to the present invention, it is possible to accurately predict degradation of a reinforced concrete structure buried in the ground.

BRIEF DESCRIPTION OF DRAWINGS

FIG. 4A is a diagram illustrating an example of the relationship between time and temperature difference and corrosion current.

FIG. 4B is a diagram illustrating an example of the relationship between time and temperature difference and corrosion current.

FIG. 8 is a diagram illustrating an example of the relationship between underground depth and corrosion rate of reinforcing steel.

DESCRIPTION OF EMBODIMENTS

One embodiment of the present invention will be described in detail below with reference to the drawings.

<Degradation Predicting Method>

A degradation predicting method according to the present embodiment will be described with reference to FIG. 1.

Figure 1:
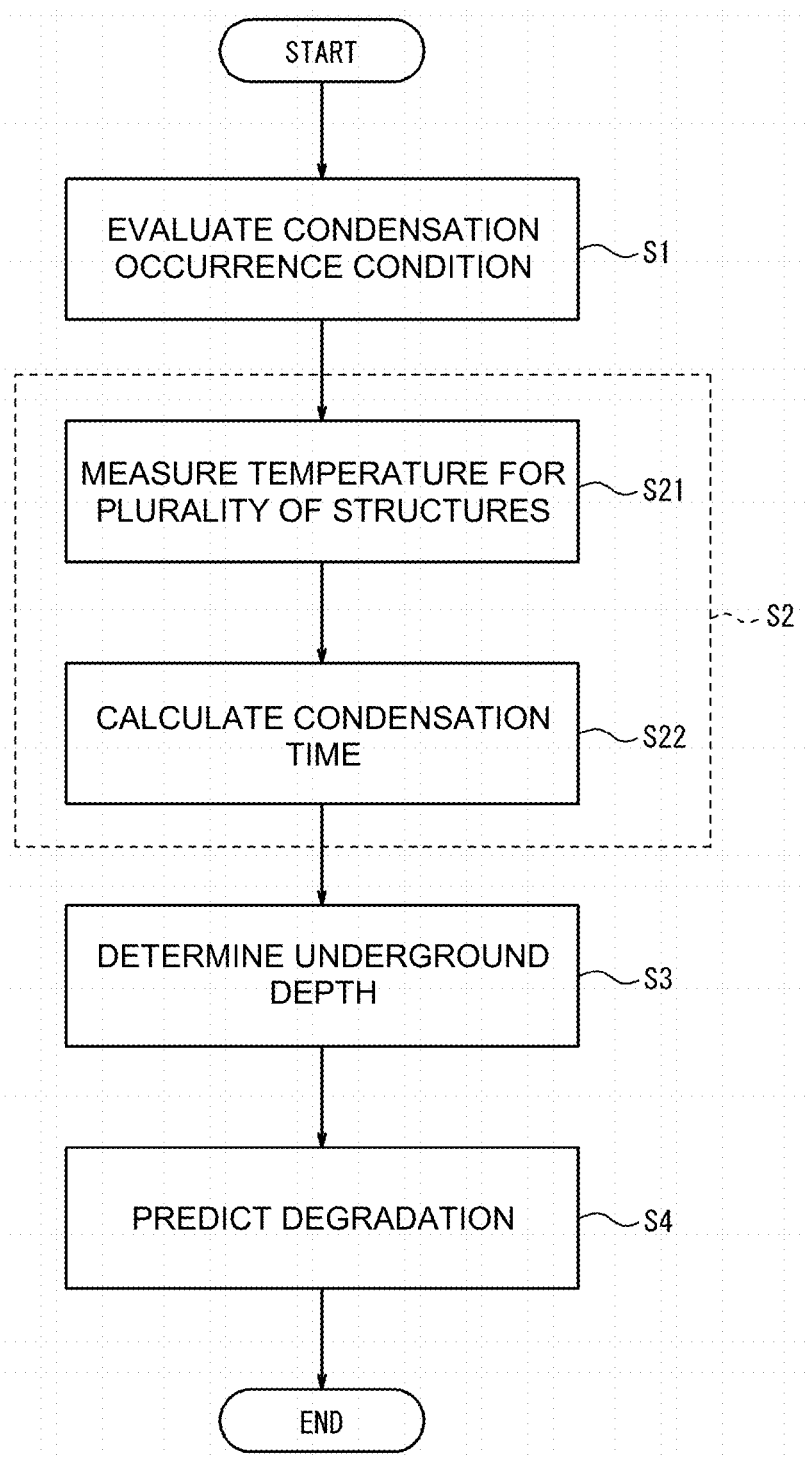
FIG. 1 is a flowchart illustrating an example of a method of predicting degradation of a reinforced concrete structure buried in the ground according to one embodiment of the present invention.

As shown in FIG. 1, the degradation predicting method according to the present embodiment is a method of predicting degradation of a reinforced concrete structure buried in the ground, including a condensation occurrence condition evaluating step (step S1), a condensation time calculating step (step S2), a underground depth determining step (step S3), and a degradation predicting step (step S4).

Examples of the reinforced concrete structure buried in the ground include a manhole, a hand hole, a shield tunnel, a sludge storage tank, and the like. The present embodiment will be described by using an example in which a manhole is applied as the reinforced concrete structure buried in the ground.

Figure 2:
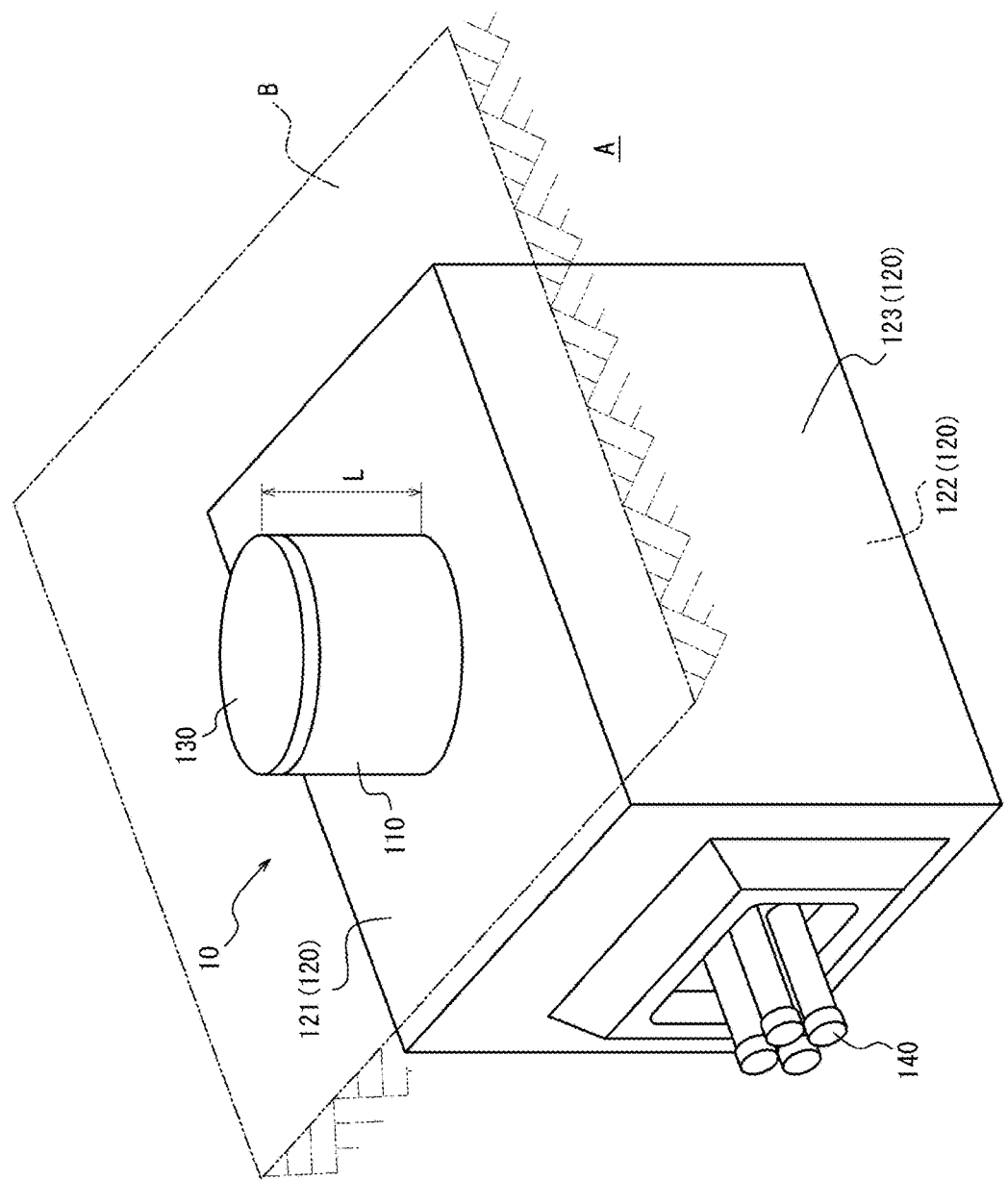
FIG. 2 is a diagram illustrating an example of the structure of a reinforced concrete structure buried in the ground according to the one embodiment of the present invention.

The structure of a manhole 10 will now be briefly described with reference to FIG. 2. The manhole 10 is a space for a worker to perform an inspection, repair, maintenance, and the like of communication cables and the like, and is buried in the ground A.

The manhole 10 includes a neck portion 110, a housing 120, a steel lid 130, and a pipeline 140. The housing 120 includes an upper floor slab 121, a lower floor slab 122, and a side wall portion 123, and is made of reinforced concrete. The neck portion 110 has a substantially cylindrical shape and has an internal space. The underground depth, L, of the manhole 10 indicates the distance between the ground surface, B, and the upper floor slab 121 in the ground, A, and is equal to the length of the neck portion 110. The housing 120 has a substantially cuboidal shape and has an internal space. A through hole connecting to the pipeline 140 is formed in the side wall portion 123 of the housing 120, and the through hole communicates the internal space of the housing 120 and the internal space of the pipeline 140 with each other. The steel lid 130 has a substantially cylindrical shape and is arranged at the opening of the manhole 10. Communication cables and the like are provided in the pipeline 140.

The degradation predicting method according to the present embodiment will be described in detail below.

[Condensation Occurrence Condition Evaluating Step (Step S1)]

In step S1, a worker evaluates a condensation occurrence condition. The condensation occurrence condition is a condition on which condensation occurs on reinforcing steel and that defines a threshold of the temperature difference between the temperature of the reinforcing steel and the internal dew point temperature of the manhole 10. For example, condensation occurs on the reinforcing steel when the temperature difference is greater than or equal to the threshold, and no condensation occurs on the reinforcing steel when the temperature difference is less than the threshold.

Figure 3A:
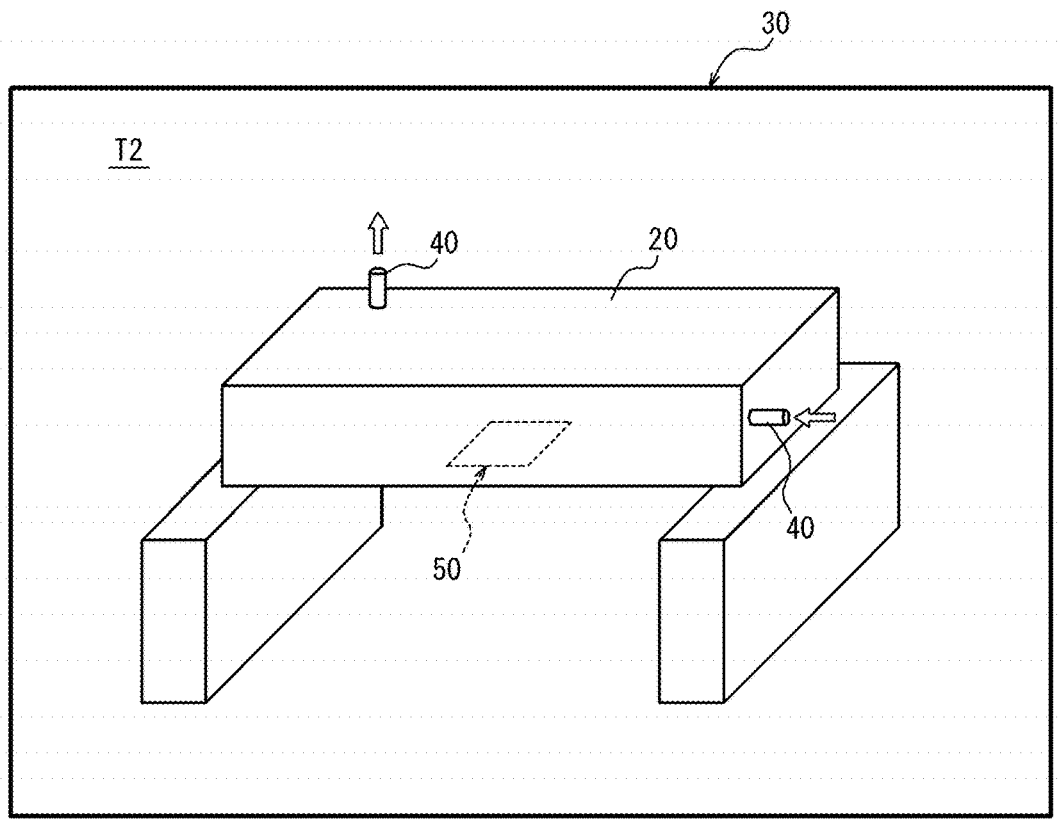
FIG. 3A is a diagram illustrating an example of an experiment system for a simulation that simulates an environment in which a reinforced concrete structure buried in the ground is provided, according to the one embodiment of the present invention.
Figure 3B:
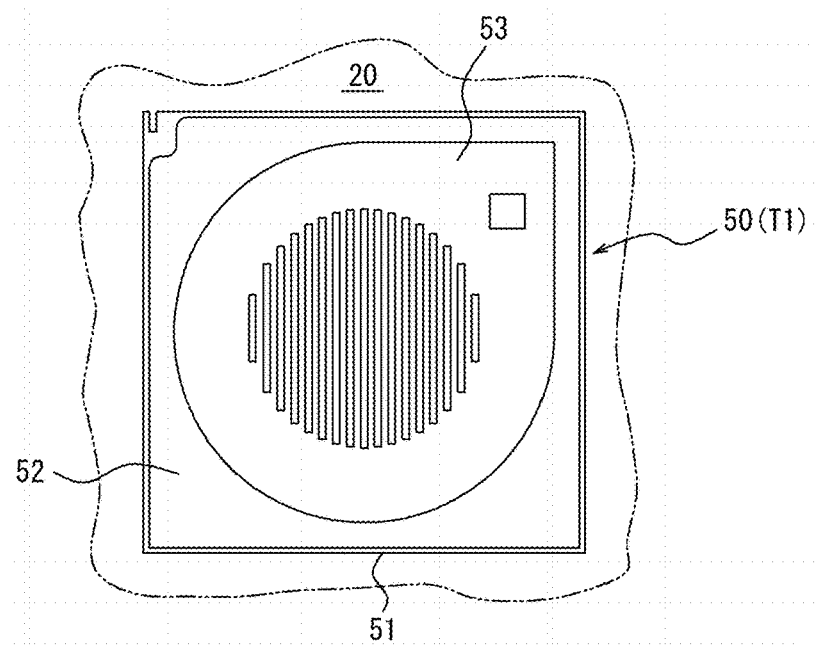
FIG. 3B is a diagram illustrating an example of a corrosion sensor stuck on a reinforced concrete structure buried in the ground according to the one embodiment of the present invention.

For example, as shown in FIG. 3, the worker performs a simulation that simulates an environment in which the manhole 10 is provided, to evaluate the condensation occurrence condition. FIG. 3A is a diagram illustrating an example of an experiment system for the simulation. FIG. 3B is a diagram illustrating an example of a corrosion sensor 50 stuck on the upper floor slab 121 of the manhole 10.

An acrylic test piece 20 corresponds to the concrete of the upper floor slab 121 of the manhole 10. The acrylic test piece 20 and the corrosion sensor 50 are provided in a constant temperature and humidity chamber 30 so as to reproduce the internal environment of the manhole 10. Note that the experiment system shown in FIG. 3A is an experiment system that assumes a steel-exposed state in which the reinforcing steel is exposed as a result of the concrete of the upper floor slab 121 of the manhole 10 being pushed out and peeling off due to corrosion expansion of the reinforcing steel. The main cause of corrosion after the exposure of the reinforcing steel of the upper floor slab 121 is condensation that occurs inside the manhole 10. Thus, the simulation performed by the worker using the experiment system that assumes the steel-exposed state makes it possible to better reproduce the mechanism of condensation occurrence and accurately evaluate the condensation occurrence condition.

First, the worker provides the acrylic test piece 20 including a pipeline 40 for circulating cooling water in the constant temperature and humidity chamber 30, and sticks the corrosion sensor 50 on the acrylic test piece 20 such as with a butyl-based double-sided tape. The corrosion sensor 50 is formed by screen-printing and fire-curing an insulating paste 52 (e.g., BN or the like) on a target metal that serves as a substrate 51 (e.g., a steel plate or the like) and lamination-printing and fire-curing a conductive paste 53 (e.g., Ag or the like) for maintaining insulation from the substrate 51 on the insulating paste 52. The corrosion sensor 50 is a sensor in which, when exposed to a predetermined environment (e.g., the internal environment of the manhole 10), water covering is formed between the substrate 51 and the conductive paste 53 such as due to condensation and a corrosion current flows. By using the corrosion sensor 50 to measure the corrosion current, the worker can grasp the degree of corrosion of the reinforcing steel, for example.

Next, the worker sets the temperature and humidity of the constant temperature and humidity chamber 30 and the temperature of the cooling water. For example, the worker sets the temperature of the constant temperature and humidity chamber 30 to 20.6° C., sets the humidity of the constant temperature and humidity chamber 30 to 80%, and sets the temperature of the cooling water to 9.7° C. Note that the worker can set the temperature and humidity of the constant temperature and humidity chamber 30 and the temperature of the cooling water as desired.

Next, the worker measures the corrosion current, the temperature, T1, of the corrosion sensor 50, the internal temperature of the constant temperature and humidity chamber 30, and the internal humidity of the constant temperature and humidity chamber 30 by varying the temperature of the cooling water by a control unit, which is not shown, while checking whether condensation occurs on the corrosion sensor 50. The temperature T1 of the corrosion sensor 50 is measured by a temperature sensor, for example. The internal temperature and humidity of the constant temperature and humidity chamber 30 are measured by a temperature and humidity sensor, for example.

Next, the worker derives the internal dew point temperature, T2, of the constant temperature and humidity chamber 30, for example, by using the Tetens equation or the like and based on the internal temperature of the constant temperature and humidity chamber 30 measured by the temperature and humidity sensor and the internal humidity of the constant temperature and humidity chamber 30 measured by the temperature and humidity sensor. The internal dew point temperature T2 of the constant temperature and humidity chamber 30 is a temperature at which the internal vapor pressure of the constant temperature and humidity chamber 30 becomes the saturated vapor pressure.

Next, the worker evaluates the condensation occurrence condition based on the corrosion current, the temperature difference, $\Delta T$, between the temperature T1 of the corrosion sensor 50 and the internal dew point temperature T2 of the constant temperature and humidity chamber 30, the presence or absence of condensation occurring on the corrosion sensor 50, and the like. For example, the worker evaluates the condensation occurrence condition based on the relationship between time and the temperature difference and the corrosion current as shown in FIG. 4, the surface state of the corrosion sensor 50 as shown in FIG. 5, and the like. When the worker inputs various pieces of data such as the corrosion current, the temperature T1 of the corrosion sensor 50, and the internal dew point temperature T2 of the constant temperature and humidity chamber 30 to a computer and perform appropriate operations, the computer generates a predetermined graph (the graph shown in FIG. 4) by using a graph creation application such as Excel (registered trademark) from Microsoft Corporation, for example, and displays the generated graph on a display unit or the like. A known computer can be applied as the computer, examples of which include a workstation, a desktop PC, a laptop PC, and the like.

Figure 5A:
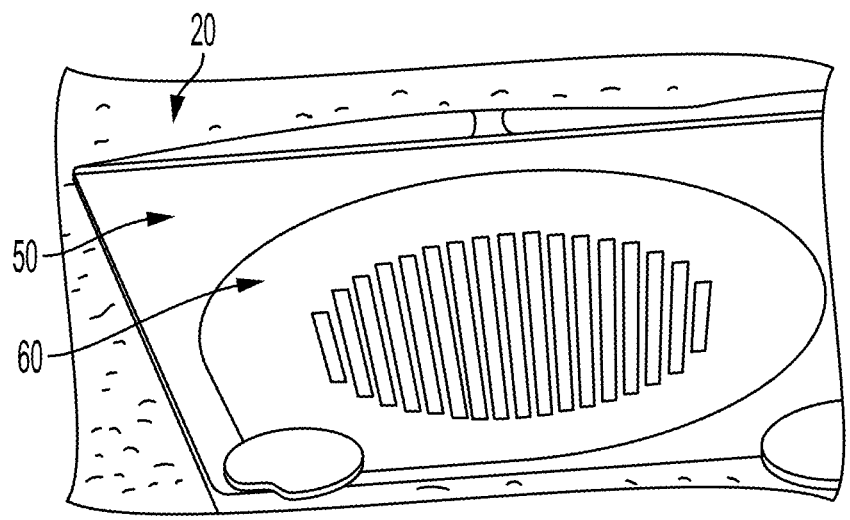
FIG. 5A is a diagram illustrating an example of the surface state of the corrosion sensor.
Figure 5B:
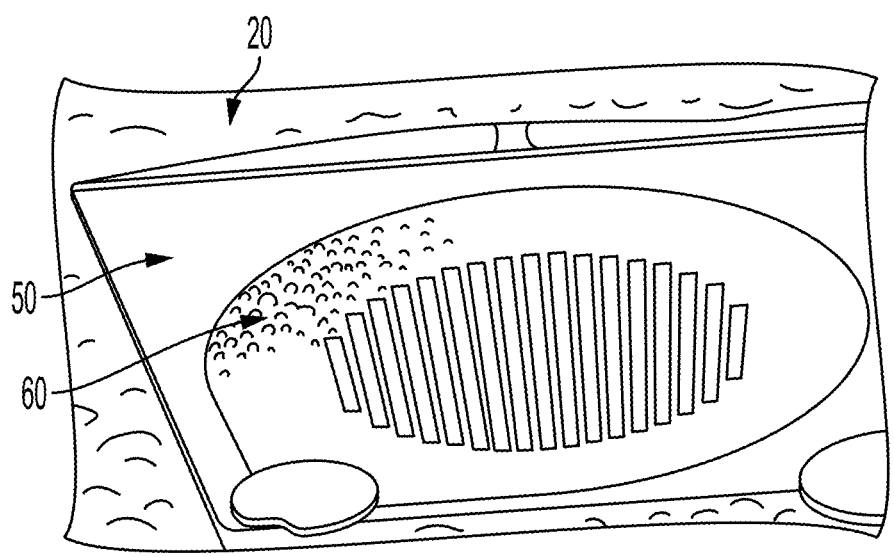
FIG. 5B is a diagram illustrating an example of the surface state of the corrosion sensor.

FIG. 4A is a graph illustrating an example of the relationship between time and the temperature difference and the corrosion current in a first simulation. The horizontal axis indicates time t [hour]. The left-side vertical axis indicates the temperature difference ΔT [° C.]. The right-side vertical axis indicates the corrosion current, I [µA]. The black dots indicate the temperature difference ΔT [° C.], and the white dots indicate the corrosion current I [µA]. FIG. 5A is a diagram illustrating an example of the surface state of the corrosion sensor 50 after 6 hours have elapsed. FIG. 5B is a diagram illustrating an example of the surface state of the corrosion sensor 50 after 15 hours have elapsed.

As shown in FIG. 4A, the temperature difference ΔT increases from about 1.25° C. to about 2.00° C. during a time period from the start of the test to when six hours have elapsed, and is maintained in a range of about 2.00° C. to about 2.50° C. during a time period from when six hours have elapsed to the end of the test. The corrosion current I is maintained at about $1.0 \times 10^{-4}$ µA during a time period from the start of the test to when six hours have elapsed, and increases from about $1.0 \times 10^{-4}$ µA to about $1.0 \times 10^{-2}$ µA during a time period from when six hours have elapsed to the end of the test.

As shown in FIG. 5A, from the start of the test to when six hours have elapsed, minute water droplets 60 are formed on the surface of the corrosion sensor 50. Since the particle diameter of the water droplets 60 is less than 1 mm, it is considered that no condensation is occurring in this experiment. On the other hand, as shown in FIG. 5B, from the start of the test to when 15 hours have elapsed, large water droplets 60 are formed on the surface of the corrosion sensor 50. The particle diameter of the water droplets 60 is several millimeters or more.

It can be seen from FIG. 4A and FIG. 5 that substantially no condensation occurs on the corrosion sensor 50 when the corrosion current I is at about $1.0 \times 10^{-4}$ µA, and condensation occurs on the corrosion sensor 50 when the corrosion current I is at about $1.0 \times 10^{-2}$ µA. It can also be seen from FIG. 4A and FIG. 5 that a threshold of corrosion current I that defines whether condensation occurs on the corrosion sensor 50 is about $1.0 \times 10^{-4}$ µA.

FIG. 4B is a graph illustrating an example of the relationship between time and the temperature difference and the corrosion current in a second simulation. The horizontal axis indicates time t [hour]. The left-side vertical axis indicates the temperature difference ΔT [° C.]. The right-side vertical axis indicates the corrosion current I [µA]. The black dots indicate the temperature difference ΔT [° C.], and the white dots indicate the corrosion current I [µA].

As shown in FIG. 4B, the temperature difference ΔT increases from about 0.50° C. to about 1.25° C. during a time period from the start of the test to when eight hours have elapsed, and is maintained in a range of about 1.00° C. to about 1.25° C. during a time period from when eight hours have elapsed to the end of the test. The corrosion current I does not flow (at 0 µA) during a time period from the start of the test to when eight hours have elapsed, and is maintained at about $1.0 \times 10^{-4}$ µA during a time period from when eight hours have elapsed to the end of the test.

It can be seen from FIG. 4B and FIG. 5 that the temperature difference ΔT for when the corrosion current I is at about $1.0 \times 10^{-4}$ µA is maintained in a range of about 1.00° C. to about 1.25° C. and there is substantially no change. That is, it can be seen that the condition on which condensation occurs on the corrosion sensor 50 is that the temperature difference ΔT between the temperature T1 of the corrosion sensor 50 and the internal dew point temperature T2 of the constant temperature and humidity chamber 30 is 1.0° C. or more.

Thus, from the above-described experimental results of the simulation that simulates an environment in which the manhole 10 is provided, the worker can evaluate that condensation occurs on the reinforcing steel when the temperature difference between the temperature of the reinforcing steel and the internal dew point temperature of the manhole 10 is 1.0° C. or more and no condensation occurs on the reinforcing steel when the temperature difference is less than 1.0° C. That is, the worker can evaluate that the condensation occurrence condition on which condensation occurs on the reinforcing steel is that the temperature difference ΔT between the temperature of the reinforcing steel and the internal dew point temperature of the manhole 10 is 1.0° C. or more.

Note that step S1 may be performed by the worker as described above, or the computer may extract appropriate data from a storage unit based on various pieces of data input by the worker to perform step S1 according to a predetermined program.

[Condensation Time Calculating Step (Step S2)]

The condensation time calculating step (step S2) specifically includes a temperature measuring step (step S21) and a condensation time calculating step (step S22).

<<Temperature Measuring Step (Step S21)>>

In step S21, for each of a plurality of manholes, the worker measures the temperature of the reinforcing steel and the internal temperature of the manhole 10.

For example, the worker uses, as the plurality of manholes, 22 manholes 10 provided in five regions in different climate divisions (e.g., Hokkaido, Akita Prefecture, Ibaraki Prefecture, Gifu Prefecture, and Okinawa Prefecture). For example, the worker uses three manholes provided in Hokkaido and having neck portion 110 lengths (underground depths L) of 50 cm, 60 cm, and 125 cm, five manholes provided in Akita Prefecture and having neck portion 110 lengths of 50 cm, 55 cm, 120 cm, 135 cm, and 145 cm, six manholes provided in Ibaraki Prefecture and having neck portion 110 lengths of 45 cm, 50 cm, 65 cm, 75 cm, 100 cm, and 110 cm, five manholes provided in Gifu Prefecture and having neck portion 110 lengths of 70 cm, 80 cm, 105 cm, 140 cm, and 180 cm, and three manholes provided in Okinawa Prefecture and having neck portion 110 lengths of 77 cm, 90 cm, and 115 cm. Note that the number of manholes 10 used by the worker for the measurement and the regions where the manholes 10 used for the measurement are provided are not particularly limited.

Figure 6:
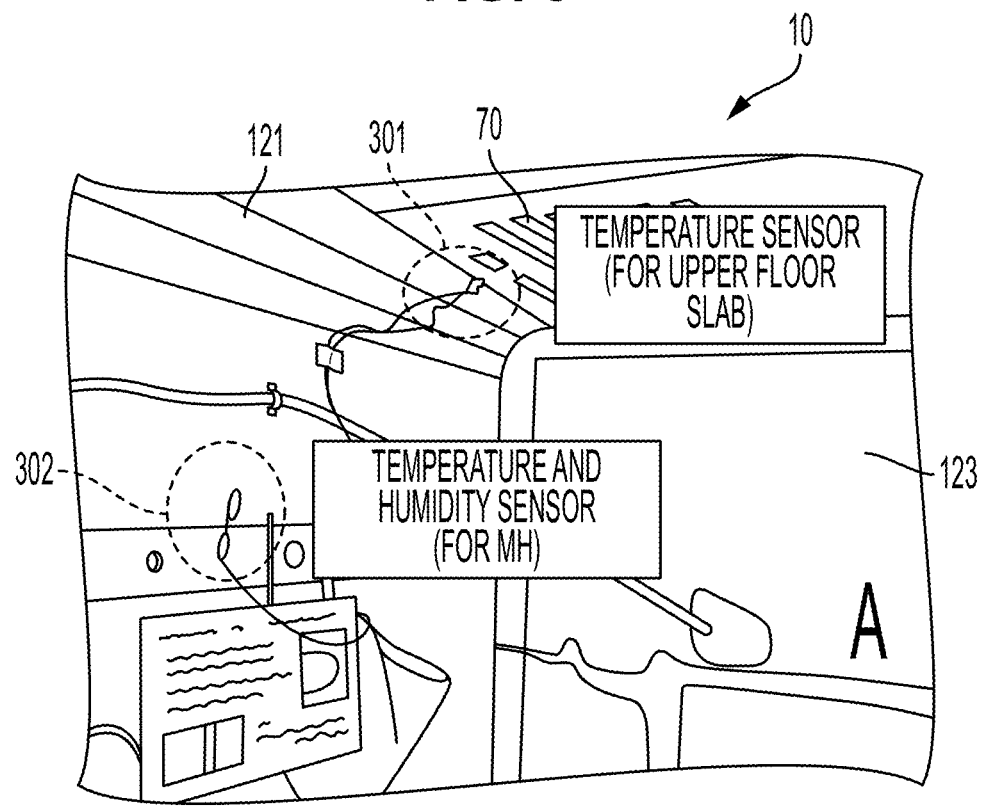
FIG. 6 is a diagram illustrating an example of an experiment system for temperature measurement in a reinforced concrete structure buried in the ground according to the one embodiment of the present invention.

As shown in FIG. 6, the worker sticks the reinforcing steel 70 on the upper floor slab 121 of the manhole 10 and measures the temperature of the reinforcing steel 70 using a temperature sensor 301, for example. A known temperature sensor such as a thermocouple can be used as the temperature sensor 301, for example. The worker measures the temperature of the reinforcing steel 70 for a measurement period of one year and at a measurement interval of one hour, for example. The method in which the worker measures the temperature of the reinforcing steel is not particularly limited, and a known method can be applied. Note that the experimental equipment shown in FIG. 6 also assumes the steel-exposed state.

The worker also measures the internal temperature of the manhole 10 using a temperature and humidity sensor 302, for example. A known temperature and humidity sensor such as a capacitive-type sensor or a resistive-type sensor can be used as the temperature and humidity sensor 302, for example. The worker measures the internal temperature of the manhole 10 for a measurement period of one year and at a measurement interval of one hour, for example. The method in which the worker measures the internal temperature of the manhole 10 is not particularly limited, and a known method can be applied. The worker may also measure the internal humidity of the manhole 10 in addition to the internal temperature of the manhole 10. In this manner, the worker can derive the internal dew point temperature of the manhole 10 based on the temperature and humidity, and therefore the degradation prediction accuracy of the degradation predicting method according to the present embodiment can be improved.

Note that step S21 may be performed by the worker as described above. In step S21, it is also possible that the computer is connected to the temperature sensor 301 and the temperature and humidity sensor 302 in a wired or wireless manner and the computer controls the temperature sensor 301 and the temperature and humidity sensor 302 so as to automatically measure the temperature of the reinforcing steel 70 or the internal temperature (or dew point temperature) of the manhole 10.

<<Condensation Time Calculating Step (Step S22)>>

In step S22, the worker inputs, to the computer, various pieces of data such as the condensation occurrence condition, the temperature of the reinforcing steel of each of the plurality of manholes, the internal temperature of each of the plurality of manholes. The computer calculates the temperature difference between the temperature of the reinforcing steel and the internal temperature of the manhole 10, and calculates a condensation time, which is a total time in which condensation occurs on the reinforcing steel 70, based on the temperature difference and the condensation occurrence condition.

For example, for a manhole (MH1) provided in Hokkaido and having a neck portion 110 length of 50 cm, the computer calculates the temperature difference (the difference between the internal temperature of MH1 and the temperature of the reinforcing steel 70 stuck on the upper floor slab 121 of MH1) during the measurement period (e.g., one year) at every measurement interval (e.g., one hour). The computer then adds up the time in which the temperature difference is 1.0° C. or more, and calculates the condensation time of MH1 as 2600 hours (about 108 days).

For example, for a manhole (MH2) provided in Hokkaido and having a neck portion 110 length of 60 cm, the computer calculates the temperature difference (the difference between the internal temperature of MH2 and the temperature of the reinforcing steel 70 stuck on the upper floor slab 121 of MH2) during the measurement period (e.g., one year) at every measurement interval (e.g., one hour). The computer then adds up the time in which the temperature difference is 1.0° C. or more, and calculates the condensation time of MH2 as 1750 hours (about 73 days).

For example, for a manhole (MH3) provided in Hokkaido and having a neck portion 110 length of 125 cm, the computer calculates the temperature difference (the difference between the internal temperature of MH3 and the temperature of the reinforcing steel 70 stuck on the upper floor slab 121 of MH3) during the measurement period (e.g., one year) at every measurement interval (e.g., one hour). The computer then adds up the time in which the temperature difference is 1.0° C. or more, and calculates the condensation time of MH3 as 0 hours.

For example, for a manhole (MH4) provided in Akita Prefecture and having a neck portion 110 length of 50 cm, the computer calculates the temperature difference (the difference between the internal temperature of MH4 and the temperature of the reinforcing steel 70 stuck on the upper floor slab 121 of MH4) during the measurement period (e.g., one year) at every measurement interval (e.g., one hour). The computer then adds up the time in which the temperature difference is 1.0° C. or more, and calculates the condensation time of MH4 as 800 hours (about 33 days).

For example, for a manhole (MH5) provided in Akita Prefecture and having a neck portion 110 length of 55 cm, the computer calculates the temperature difference (the difference between the internal temperature of MH5 and the temperature of the reinforcing steel 70 stuck on the upper floor slab 121 of MH5) during the measurement period (e.g., one year) at every measurement interval (e.g., one hour). The computer then adds up the time in which the temperature difference is 1.0° C. or more, and calculates the condensation time of MH5 as 400 hours (about 17 days).

For example, for a manhole (MH6) provided in Akita Prefecture and having a neck portion 110 length of 120 cm, the computer calculates the temperature difference (the difference between the internal temperature of MH6 and the temperature of the reinforcing steel 70 stuck on the upper floor slab 121 of MH6) during the measurement period (e.g., one year) at every measurement interval (e.g., one hour). The computer then adds up the time in which the temperature difference is 1.0° C. or more, and calculates the condensation time of MH6 as 0 hours.

For example, for a manhole (MH7) provided in Akita Prefecture and having a neck portion 110 length of 135 cm, the computer calculates the temperature difference (the difference between the internal temperature of MH7 and the temperature of the reinforcing steel 70 stuck on the upper floor slab 121 of MH7) during the measurement period (e.g., one year) at every measurement interval (e.g., one hour). The computer then adds up the time in which the temperature difference is 1.0° C. or more, and calculates the condensation time of MH7 as 0 hours.

For example, for a manhole (MH8) provided in Akita Prefecture and having a neck portion 110 length of 145 cm, the computer calculates the temperature difference (the difference between the internal temperature of MH8 and the temperature of the reinforcing steel 70 stuck on the upper floor slab 121 of MH8) during the measurement period (e.g., one year) at every measurement interval (e.g., one hour). The computer then adds up the time in which the temperature difference is 1.0° C. or more, and calculates the condensation time of MH8 as 0 hours.

For example, for a manhole (MH9) provided in Ibaraki Prefecture and having a neck portion 110 length of 45 cm, the computer calculates the temperature difference (the difference between the internal temperature of MH9 and the temperature of the reinforcing steel 70 stuck on the upper floor slab 121 of MH9) during the measurement period (e.g., one year) at every measurement interval (e.g., one hour). The computer then adds up the time in which the temperature difference is 1.0° C. or more, and calculates the condensation time of MH9 as 100 hours (about 4 days).

For example, for a manhole (MH10) provided in Ibaraki Prefecture and having a neck portion 110 length of 50 cm, the computer calculates the temperature difference (the difference between the internal temperature of MH10 and the temperature of the reinforcing steel 70 stuck on the upper floor slab 121 of MH10) during the measurement period (e.g., one year) at every measurement interval (e.g., one hour). The computer then adds up the time in which the temperature difference is 1.0° C. or more, and calculates the condensation time of MH10 as 400 hours (about 17 days).

For example, for a manhole (MH11) provided in Ibaraki Prefecture and having a neck portion 110 length of 65 cm, the computer calculates the temperature difference (the difference between the internal temperature of MH11 and the temperature of the reinforcing steel 70 stuck on the upper floor slab 121 of MH11) during the measurement period (e.g., one year) at every measurement interval (e.g., one hour). The computer then adds up the time in which the temperature difference is 1.0° C. or more, and calculates the condensation time of MH11 as 700 hours (about 29 days).

For example, for a manhole (MH12) provided in Ibaraki Prefecture and having a neck portion 110 length of 75 cm, the computer calculates the temperature difference (the difference between the internal temperature of MH12 and the temperature of the reinforcing steel 70 stuck on the upper floor slab 121 of MH12) during the measurement period (e.g., one year) at every measurement interval (e.g., one hour). The computer then adds up the time in which the temperature difference is 1.0° C. or more, and calculates the condensation time of MH12 as 600 hours (about 25 days).

For example, for a manhole (MH13) provided in Ibaraki Prefecture and having a neck portion 110 length of 100 cm, the computer calculates the temperature difference (the difference between the internal temperature of MH13 and the temperature of the reinforcing steel 70 stuck on the upper floor slab 121 of MH13) during the measurement period (e.g., one year) at every measurement interval (e.g., one hour). The computer then adds up the time in which the temperature difference is 1.0° C. or more, and calculates the condensation time of MH13 as 0 hours.

For example, for a manhole (MH14) provided in Ibaraki Prefecture and having a neck portion 110 length of 110 cm, the computer calculates the temperature difference (the difference between the internal temperature of MH14 and the temperature of the reinforcing steel 70 stuck on the upper floor slab 121 of MH14) during the measurement period (e.g., one year) at computer then adds up the time in which the temperature difference is 1.0° C. or more, and calculates the condensation time of MH14 as 0 hours.

For example, for a manhole (MH15) provided in Gifu Prefecture and having a neck portion 110 length of 70 cm, the computer calculates the temperature difference (the difference between the internal temperature of MH15 and the temperature of the reinforcing steel 70 stuck on the upper floor slab 121 of MH15) during the measurement period (e.g., one year) at every measurement interval (e.g., one hour). The computer then adds up the time in which the temperature difference is 1.0° C. or more, and calculates the condensation time of MH15 as 1600 hours.

For example, for a manhole (MH16) provided in Gifu Prefecture and having a neck portion 110 length of 80 cm, the computer calculates the temperature difference (the difference between the internal temperature of MH16 and the temperature of the reinforcing steel 70 stuck on the upper floor slab 121 of MH16) during the measurement period (e.g., one year) at every measurement interval (e.g., one hour). The computer then adds up the time in which the temperature difference is 1.0° C. or more, and calculates the condensation time of MH16 as 1100 hours (about 46 days).

For example, for a manhole (MH17) provided in Gifu Prefecture and having a neck portion 110 length of 105 cm, the computer calculates the temperature difference (the difference between the internal temperature of MH17 and the temperature of the reinforcing steel 70 stuck on the upper floor slab 121 of MH17) during the measurement period (e.g., one year) at every measurement interval (e.g., one hour). The computer then adds up the time in which the temperature difference is 1.0° C. or more, and calculates the condensation time of MH17 as 0 hours.

For example, for a manhole (MH18) provided in Gifu Prefecture and having a neck portion 110 length of 140 cm, the computer calculates the temperature difference (the difference between the internal temperature of MH18 and the temperature of the reinforcing steel 70 stuck on the upper floor slab 121 of MH18) during the measurement period (e.g., one year) at every measurement interval (e.g., one hour). The computer then adds up the time in which the temperature difference is 1.0° C. or more, and calculates the condensation time of MH18 as 0 hours.

For example, for a manhole (MH19) provided in Gifu Prefecture and having a neck portion 110 length of 180 cm, the computer calculates the temperature difference (the difference between the internal temperature of MH19 and the temperature of the reinforcing steel 70 stuck on the upper floor slab 121 of MH19) during the measurement period (e.g., one year) at computer then adds up the time in which the temperature difference is 1.0° C. or more, and calculates the condensation time of MH19 as 0 hours.

For example, for a manhole (MH20) provided in Okinawa Prefecture and having a neck portion 110 length of 77 cm, the computer calculates the temperature difference (the difference between the internal temperature of MH20 and the temperature of the reinforcing steel 70 stuck on the upper floor slab 121 of MH20) during the measurement period (e.g., one year) at every measurement interval (e.g., one hour). The computer then adds up the time in which the temperature difference is 1.0° C. or more, and calculates the condensation time of MH20 as 900 hours (about 38 days).

For example, for a manhole (MH21) provided in Okinawa Prefecture and having a neck portion 110 length of 90 cm, the computer calculates the temperature difference (the difference between the internal temperature of MH21 and the temperature of the reinforcing steel 70 stuck on the upper floor slab 121 of MH21) during the measurement period (e.g., one year) at every measurement interval (e.g., one hour). The computer then adds up the time in which the temperature difference is 1.0° C. or more, and calculates the condensation time of MH21 as 100 hours (about 4 days).

For example, for a manhole (MH22) provided in Okinawa Prefecture and having a neck portion 110 length of 115 cm, the computer calculates the temperature difference (the difference between the internal temperature of MH22 and the temperature of the reinforcing steel 70 stuck on the upper floor slab 121 of MH22) during the measurement period (e.g., one year) at every measurement interval (e.g., one hour). The computer then adds up the time in which the temperature difference is 1.0° C. or more, and calculates the condensation time of MH22 as 50 hours (about 2 days).

[Underground Depth Determining Step (Step S3)]

In step S3, the worker determines a threshold of condensation time at which reinforcing steel 70 is less prone to corrosion based on the relationship between the condensation times calculated by the computer and the manhole underground depths, and determines a threshold of underground depth at which manholes are less prone to degradation based on the threshold. When the worker inputs various pieces of data such as the underground depths of the plurality of manholes (e.g., MH1 to MH22) and the condensation times of the plurality of manholes (e.g., MH1 to MH22) to the computer and perform appropriate operations, the computer generates a predetermined graph (the graph shown in FIG. 7) by using a graph creation application such as Excel (registered trademark) from Microsoft Corporation, for example, and displays the generated graph on the display unit or the like.

Figure 7:
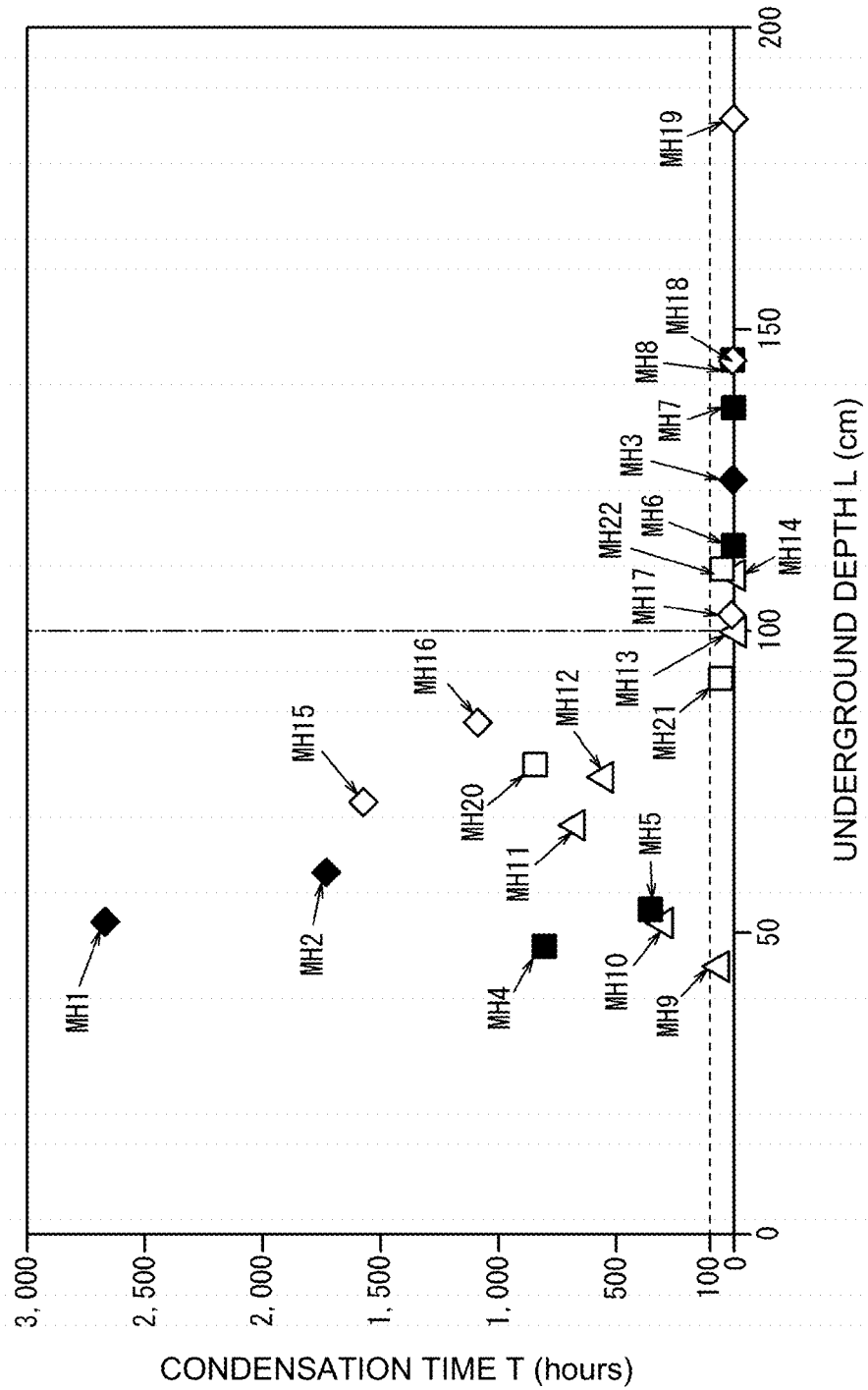
FIG. 7 is a diagram illustrating an example of the relationship between underground depth and condensation time.

FIG. 7 is a graph illustrating the relationship between the underground depth and the condensation time. The horizontal axis indicates the underground depth L [cm]. The vertical axis indicates the condensation time T [hours]. The black diamonds indicate three manholes (MH1, MH2, and MH3) provided in Hokkaido. The black squares indicate five manholes (MH4, MH5, MH6, MH7, and MH8) provided in Akita Prefecture. The outlined triangles indicate six manholes (MH9, MH10, MH11, MH12, MH13, and MH14) provided in Ibaraki Prefecture. The outlined diamonds indicate five manholes (MH15, MH16, MH17, MH18, and MH19) provided in Gifu Prefecture. The outlined squares indicate three manholes (MH20, MH21, and MH22) provided in Okinawa Prefecture.

First, the worker determines the threshold of condensation time at which reinforcing steel 70 is less prone to corrosion based on the graph shown in FIG. 7.

It can be seen from FIG. 7 that the condensation time T tends to decrease as the manhole underground depth L increases, and the condensation time T tends to increase as the manhole underground depth L decreases. It can also be seen that there are an increased number of manholes having a large underground depth L in a range where the condensation time T is 100 hours or less.

Thus, the worker can evaluate that reinforcing steel 70 is less prone to corrosion if the condensation time T is 100 hours or less, and reinforcing steel 70 is prone to corrosion if the condensation time T is more than 100 hours. That is, the worker can determine the threshold of condensation time at which reinforcing steel 70 is less prone to corrosion as 100 hours. Note that the worker can determine the threshold of condensation time at which reinforcing steel 70 is less prone to corrosion as desired.

Next, the worker determines the threshold of underground depth at which manholes are less prone to degradation based on the graph shown in FIG. 7 and the threshold of condensation time at which reinforcing steel 70 is less prone to corrosion (e.g., 100 hours).

It can be seen from FIG. 7 that the number of manholes for which the condensation time T is 100 hours or less are 12, i.e., MH3, MH6, MH7, MH8, MH9, MH13, MH14, MH17, MH18, MH19, MH21, and MH22. For these 12 manholes, it can be seen that the number of manholes tends to increase as the underground depth L of the manhole increases, and the number of manholes tends to decrease as the underground depth L of the manhole decreases. It can also be seen that there are an increased number of manholes in a range where the underground depth L is 100 cm or more.

Thus, the worker can evaluate that manholes are less prone to degradation when the manhole underground depth L is 100 cm or more, and manholes are prone to degradation when the manhole underground depth L is less than 100 cm. Thus, the worker can determine the threshold of underground depth at which manholes are less prone to degradation as 100 cm. Note that the worker can determine the threshold of underground depth at which manholes are less prone to degradation as desired.

Specifically, in order to obtain a reliable value as the threshold of underground depth at which manholes are less prone to degradation, the worker may select MH13 having the third smallest underground depth L among the 12 manholes (MH3, MH6, MH7, MH8, MH9, MH13, MH14, MH17, MH18, MH19, MH21, and MH22), and determine the threshold of underground depth at which manholes are less prone to degradation as 100 cm, which is the underground depth of MH13. Note that the worker may also select the manhole MH17 having the fourth smallest underground depth L among the 12 manholes, and determine the threshold of underground depth at which manholes are less prone to degradation as 105 cm, which is the underground depth of MH17, for example. The worker may also select the manhole MH14 having the fifth smallest underground depth L among the 12 manholes, and determine the threshold of underground depth at which manholes are less prone to degradation as 110 cm, which is the underground depth of MH14, for example. The worker can select a manhole expected to result in a reliable value as the threshold of underground depth at which manholes are less prone to degradation as desired.

Alternatively, the worker can also determine the threshold of underground depth at which manholes are less prone to degradation for each of regions in different climate divisions.

For example, the worker may select, from MH1 to MH3 provided in Hokkaido, MH3 of which the condensation time T is 100 hours or less, and determine the threshold of underground depth at which manholes provided in Hokkaido are less prone to degradation as 125 cm, which is the underground depth of MH3.

The worker may also select, from MH4 to MH8 provided in Akita Prefecture, MH7 having the second smallest underground depth L among the three manholes (MH6, MH7, and MH8) of which the condensation time T is 100 hours or less, and determine the threshold of underground depth at which manholes provided in Akita Prefecture are less prone to degradation as 135 cm, which is the underground depth of MH7, for example.

The worker may also select, from MH9 to MH14 provided in Ibaraki Prefecture, MH14 having the third smallest underground depth L among the three manholes (MH9, MH13, and MH14) of which the condensation time T is 100 hours or less, and determine the threshold of underground depth at which manholes provided in Ibaraki Prefecture are less prone to degradation as 110 cm, which is the underground depth of MH14, for example.

The worker may also select, from MH15 to MH19 provided in Gifu Prefecture, MH17 having the smallest underground depth L among the three manholes (MH17, MH18, and MH19) of which the condensation time T is 100 hours or less, and determine the threshold of underground depth at which manholes provided in Gifu Prefecture are less prone to degradation as 105 cm, which is the underground depth of MH17, for example.

The worker may also select, from MH20 to MH22 provided in Okinawa Prefecture, MH22 having the second smallest underground depth L among the two manholes (MH21 and MH22) of which the condensation time T is 100 hours or less, and determine the threshold of underground depth at which manholes provided in Okinawa Prefecture are less prone to degradation as 115 cm, which is the underground depth of MH22, for example.

Note that step S3 may be performed based on experimental results on a plurality of manholes (e.g., MH1 to MH22) randomly extracted by the worker as described above, or may be performed based on experimental results on a plurality of manholes intentionally extracted by the worker by excluding manholes provided in special environments.

[Degradation Predicting Step (Step S4)]

In step S4, the worker predicts degradation of a prediction-target manhole based on the threshold of underground depth at which manholes are less prone to degradation. For example, in the case where the threshold is 100 cm, the worker predicts that the prediction-target manhole is prone to degradation if the underground depth of the prediction-target manhole is less than 100 cm and predicts that the prediction-target manhole is less prone to degradation if the underground depth of the prediction-target manhole is 100 cm or more.

For example, if the underground depth of the prediction-target manhole is 10 cm, which is less than the threshold of underground depth at which manholes are less prone to degradation, the worker predicts that the prediction-target manhole is prone to degradation. For example, if the underground depth of the prediction-target manhole is 50 cm, which is less than the threshold of underground depth at which manholes are less prone to degradation, the worker predicts that the prediction-target manhole is prone to degradation. For example, if the underground depth of the prediction-target manhole is 120 cm, which is greater than or equal to the threshold of underground depth at which manholes are less prone to degradation, the worker predicts that the prediction-target manhole is less prone to degradation.

Note that step S4 may be performed by the worker as described above, or the computer may extract appropriate data from the storage unit based on various pieces of data input by the worker to perform step S4 according to a predetermined program.

In the degradation predicting method according to the present embodiment, the degradation of the prediction-target manhole is predicted based on the threshold of underground depth at which manholes are less prone to degradation. In this manner, the accuracy of predicting the degradation of the prediction-target manhole can be improved as compared to the conventional, qualitative prediction that there is a tendency that manholes are less prone to degradation as their underground depth is larger.

The degradation predicting method according to the present embodiment can be applied to a plurality of manholes provided in different environments to predict degradation of each manhole, so that the worker can perform maintenance at appropriate periods in response to the degradation of each manhole and appropriately allocate limited maintenance resources for the plurality of manholes. As a result, it is possible to appropriately maintain the health of the plurality of manholes provided in different environments.

<Verification of Degradation Predicting Method>

The worker applies the degradation predicting method according to the present embodiment to a plurality of manholes to predict degradation of each manhole and verifies the accuracy of the prediction.

First, the worker calculates corrosion rates of reinforcing steel for the plurality of manholes. For example, the worker uses, as the plurality of manholes, a manhole (mh1) provided in Hokkaido and having a neck portion 110 length of 52 cm, a manhole (mh2) provided in Hokkaido and a neck portion 110 length of 60 cm, a manhole (mh3) provided in Hokkaido and having a neck portion 110 length of 79 cm, a manhole (mh4) provided in Hokkaido and having a neck portion 110 length of 125 cm, a manhole (mh5) provided in Akita Prefecture and having a neck portion 110 length of 48 cm, a manhole (mh6) provided in Akita Prefecture and having a neck portion 110 length of 53 cm, a manhole (mh7) provided in Akita Prefecture and having a neck portion 110 length of 57 cm, a manhole (mh8) provided in Akita Prefecture and having a neck portion 110 length of 64 cm, a manhole (mh9) provided in Ibaraki Prefecture and having a neck portion 110 length 45 cm, a manhole (mh10) provided in Ibaraki Prefecture and having a neck portion 110 length of 52 cm, a manhole (mh11) provided in Ibaraki Prefecture and having a neck portion 110 length of 58 cm, a manhole (mh12) provided in Ibaraki Prefecture and having a neck portion 110 length of 68 cm, a manhole (mh13) provided in Ibaraki Prefecture and having a neck portion 110 length of 76 cm, a manhole (mh14) provided in Gifu Prefecture and having a neck portion 110 length of 55 cm, a manhole (mh15) provided in Gifu Prefecture and having a neck portion 110 length of 72 cm, a manhole (mh16) provided in Gifu Prefecture and having a neck portion 110 length of 185 cm, a manhole (mh17) provided in Okinawa Prefecture and having a neck portion 110 length of 78 cm, a manhole (mh18) provided in Okinawa Prefecture and having a neck portion 110 length of 92 cm, and a manhole (mh19) provided in Okinawa Prefecture and having a neck portion 110 length of 116 cm.

The worker sticks reinforcing steel 70 on the upper floor slab 121 of each manhole 10 and measures the initial weight of the reinforcing steel 70 using a weight meter, for example. After exposure of the reinforcing steel 70 for one year (12 months), the worker retrieves the reinforcing steel 70 stuck on the upper floor slab 121, and measures the weight of the reinforcing steel 70 after the exposure using a weight meter, for example. The worker then inputs, to a computer, various pieces of data such as the initial weight of the reinforcing steel 70 and the weight of the reinforcing steel 70 after the exposure.

The computer calculates the corrosion rate, C, of the reinforcing steel based on the initial weight of the reinforcing steel 70 input by the worker and the weight of the reinforcing steel 70 after the exposure input by the worker and using a formula of {(the initial weight of the reinforcing steel−the weight of the reinforcing steel after the exposure)/the initial weight of the reinforcing steel×100}.

For mh1, the corrosion rate C of the reinforcing steel 70 is 0.23%. For mh2, the corrosion rate C of the reinforcing steel 70 is 0.25%. For mh3, the corrosion rate C of the reinforcing steel 70 is 1.16%. For mh4, the corrosion rate C of the reinforcing steel 70 is 0.05%. For mh5, the corrosion rate C of the reinforcing steel 70 is 1.15%. For mh6, the corrosion rate C of the reinforcing steel 70 is 0.85%. For mh7, the corrosion rate C of the reinforcing steel 70 is 0.45%. For mh8, the corrosion rate C of the reinforcing steel 70 is 0.05%. For mh9, the corrosion rate C of the reinforcing steel 70 is 0.46%. For mh10, the corrosion rate C of the reinforcing steel 70 is 0.06%. For mh11, the corrosion rate C of the reinforcing steel 70 is 0.60%. For mh12, the corrosion rate C of the reinforcing steel 70 is 1.05%. For mh13, the corrosion rate C of the reinforcing steel 70 is 1.00%. For mh14, the corrosion rate C of the reinforcing steel 70 is 1.10%. For mh15, the corrosion rate C of the reinforcing steel 70 is 0.50%. For mh16, the corrosion rate C of the reinforcing steel 70 is 0.05%. For mh17, the corrosion rate C of the reinforcing steel 70 is 0.90%. For mh18, the corrosion rate C of the reinforcing steel 70 is 1.00%. For mh19, the corrosion rate C of the reinforcing steel 70 is 0.16%.

Next, the worker inputs various pieces of data such as the underground depths of the plurality of manholes (e.g., mh1 to mh19) and the corrosion rates of the reinforcing steel 70 of the plurality of manholes (e.g., mh1 to mh19) to the computer and performs appropriate operations. The computer generates a predetermined graph (the graph shown in FIG. 8) by using a graph creation application such as Excel (registered trademark) from Microsoft Corporation, for example, and displays the generated graph on the display unit or the like.

FIG. 8 is a graph illustrating an example of the relationship between underground depth and corrosion rate of reinforcing steel. The horizontal axis indicates the underground depth L [cm]. The vertical axis indicates corrosion rate C of reinforcing steel (12 months) [%]. The black diamonds indicate four manholes (mh1, mh2, mh3, and mh4) provided in Hokkaido. The black squares indicate four manholes (mh5, mh6, mh7, and mh8) provided in Akita Prefecture. The outlined triangles indicate five manholes (mh9, mh10, mh11, mh12, and mh13) provided in Ibaraki Prefecture. The outlined diamonds indicate three manholes (mh14, mh15, and mh16) provided in Gifu Prefecture. The outlined squares indicate three manholes (mh17, mh18, and mh19) provided in Okinawa Prefecture.

It can be seen from FIG. 8 that the corrosion rate C of reinforcing steel tends to decrease as the underground depth L of the manhole increases, and the corrosion rate C of reinforcing steel tends to increase as the underground depth L of the manhole decreases.

Thus, the worker defines a threshold of corrosion rate C of reinforcing steel for determining degradation of manholes as 0.20%, for example. The worker determines degradation of the plurality of manholes (e.g., mh1 to mh19) based on the value of 0.20%. For example, the worker determines that a manhole is not degraded if the corrosion rate C of reinforcing steel is less than 0.20% and determined that the manhole is degraded if the corrosion rate C of reinforcing steel is 0.20% or more. Thus, the worker determines that mh4, mh8, mh9, mh10, and mh16 are not degraded. The worker also determines that mh1, mh2, mh3, mh5, mh6, mh7, mh11, mh12, mh13, mh14, mh15, mh17, mh18, and mh19 are degraded. Note that the threshold of corrosion rate C of reinforcing steel for determining degradation of manholes is not limited to 0.20% and can be defined by the worker as desired.

Next, the worker applies the degradation predicting method according to the present embodiment to the plurality of manholes (e.g., mh1 to mh19) to predict degradation of the plurality of manholes (e.g., mh1 to mh19), and verifies whether there is consistency with the above-mentioned determination results.

For mh1, since the length of the neck portion 110 (the underground depth L) of mh1 is 52 cm, which is less than 100 cm, the worker predicts that it is prone to degradation. Since the corrosion rate C of reinforcing steel of mh1 is 0.23%, which is 0.20% or more, from the above-mentioned determination results, the worker can verify that the prediction is correct.

For mh2, since the length of the neck portion 110 of mh2 is 60 cm, which is less than 100 cm, the worker predicts that it is prone to degradation. Since the corrosion rate C of reinforcing steel of mh2 is 0.25%, which is 0.20% or more, from the above-mentioned determination results, the worker can verify that the prediction is correct.

For mh3, since the length of the neck portion 110 of mh3 is 79 cm, which is less than 100 cm, the worker predicts that it is prone to degradation. Since the corrosion rate C of reinforcing steel of mh3 is 1.16%, which is 0.20% or more, from the above-mentioned determination results, the worker can verify that the prediction is correct.

For mh4, since the length of the neck portion 110 of mh4 is 125 cm, which is 100 cm or more, the worker predicts that it is less prone to degradation. Since the corrosion rate C of reinforcing steel of mh4 is 0.05%, which is less than 0.20%, from the above-mentioned determination results, the worker can verify that the prediction is correct.

For mh5, since the length of the neck portion 110 of mh5 is 48 cm, which is less than 100 cm, the worker predicts that it is prone to degradation. Since the corrosion rate C of reinforcing steel of mh5 is 1.15%, which is 0.20% or more, from the above-mentioned determination results, the worker can verify that the prediction is correct.

For mh6, since the length of the neck portion 110 of mh6 is 53 cm, which is less than 100 cm, the worker predicts that it is prone to degradation. Since the corrosion rate C of reinforcing steel of mh6 is 0.85%, which is 0.20% or more, from the above-mentioned determination results, the worker can verify that the prediction is correct.

For mh7, since the length of the neck portion 110 of mh7 is 57 cm, which is less than 100 cm, the worker predicts that it is prone to degradation. Since the corrosion rate C of reinforcing steel of mh7 is 0.45%, which is 0.20% or more, from the above-mentioned determination results, the worker can verify that the prediction is correct.

For mh8, since the length of the neck portion 110 of mh8 is 64 cm, which is less than 100 cm, the worker predicts that it is prone to degradation. However, since the corrosion rate C of reinforcing steel of mh8 is 0.05%, which is less than 0.20%, from the above-mentioned determination results, the worker cannot verify that the prediction is correct.

For mh9, since the length of the neck portion 110 of mh9 is 45 cm, which is less than 100 cm, the worker predicts that it is prone to degradation. Since the corrosion rate C of reinforcing steel of mh9 is 0.46%, which is 0.20% or more, from the above-mentioned determination results, the worker can verify that the prediction is correct.

For mh10, since the length of the neck portion 110 of mh10 is 52 cm, which is less than 100 cm, the worker predicts that it is prone to degradation. However, since the corrosion rate C of reinforcing steel of mh10 is 0.06%, which is less than 0.20%, from the above-mentioned determination results, the worker cannot verify that the prediction is correct.

For mh11, since the length of the neck portion 110 of mh11 is 58 cm, which is less than 100 cm, the worker predicts that it is prone to degradation. Since the corrosion rate C of reinforcing steel of mh11 is 0.60%, which is 0.20% or more, from the above-mentioned determination results, the worker can verify that the prediction is correct.

For mh12, since the length of the neck portion 110 of mh12 is 68 cm, which is less than 100 cm, the worker predicts that it is prone to degradation. Since the corrosion rate C of reinforcing steel of mh12 is 1.05%, which is 0.20% or more, from the above-mentioned determination results, the worker can verify that the prediction is correct.

For mh13, since the length of the neck portion 110 of mh13 is 76 cm, which is less than 100 cm, the worker predicts that it is prone to degradation. Since the corrosion rate C of reinforcing steel of mh13 is 1.00%, which is 0.20% or more, from the above-mentioned determination results, the worker can verify that the prediction is correct.

For mh14, since the length of the neck portion 110 of mh14 is 55 cm, which is less than 100 cm, the worker predicts that it is prone to degradation. Since the corrosion rate C of reinforcing steel of mh14 is 1.10%, which is 0.20% or more, from the above-mentioned determination results, the worker can verify that the prediction is correct.

For mh15, since the length of the neck portion 110 of mh15 is 72 cm, which is less than 100 cm, the worker predicts that it is prone to degradation. Since the corrosion rate C of reinforcing steel of mh15 is 0.50%, which is 0.20% or more, from the above-mentioned determination results, the worker can verify that the prediction is correct.

For mh16, since the length of the neck portion 110 of mh16 is 185 cm, which is 100 cm or more, the worker predicts that it is less prone to degradation. Since the corrosion rate C of reinforcing steel of mh16 is 0.05%, which is less than 0.20%, from the above-mentioned determination results, the worker can verify that the prediction is correct.

For mh17, since the length of the neck portion 110 of mh17 is 78 cm, which is less than 100 cm, the worker predicts that it is prone to degradation. Since the corrosion rate C of reinforcing steel of mh17 is 0.90%, which is 0.20% or more, from the above-mentioned determination results, the worker can verify that the prediction is correct.

For mh18, since the length of the neck portion 110 of mh18 is 92 cm, which is less than 100 cm, the worker predicts that it is prone to degradation. Since the corrosion rate C of reinforcing steel of mh18 is 1.00%, which is 0.20% or more, from the above-mentioned determination results, the worker can verify that the prediction is correct.

For mh19, since the length of the neck portion 110 of mh19 is 116 cm, which is 100 cm or more, the worker predicts that it is less prone to degradation. Since the corrosion rate C of reinforcing steel of mh19 is 0.16%, which is less than 0.20%, from the above-mentioned determination results, the worker can verify that the prediction is correct.

Thus, the worker's predictions that mh4, mh9, and mh16 are less prone to degradation are all verified to be correct. Although the worker's predictions that mh8 and mh10 are prone to degradation are verified to be incorrect, the worker's predictions that mh1, mh2, mh3, mh5, mh6, mh7, mh11, mh12, mh13, mh14, mh15, mh17, mh18, and mh19 are prone to degradation are verified to be correct.

From the above verifications, the degradation predicting method according to the present embodiment can accurately determine a threshold of underground depth at which a reinforced concrete structure buried in the ground is less prone to degradation. It is also possible to accurately predict degradation of the reinforced concrete structure buried in the ground.

Note that, as described above, a computer can be used as an assisting device that assists the degradation predicting method according to the present embodiment. The computer stores a program in which various processes are written in a storage unit of the computer, and causes a CPU of the computer to read and execute the program. Note that the program can be recorded on a computer-readable recording medium.

The program may also be recorded on a computer readable medium. The use of the computer readable medium allows installation on the computer. The computer readable medium on which the program is recorded may be a non-transitory recording medium. The non-transitory recording medium is not particularly limited, and may be a recording medium such as a CD-ROM or a DVD-ROM, for example.

Modified Example

In the present embodiment, in step S1, the worker performs a simulation that simulates an environment in which the manhole 10 is provided, to evaluate the condensation occurrence condition. In step S1, the worker may also perform an experiment using an actually provided manhole 10 to evaluate the condensation occurrence condition. In this case, the worker sticks a submergence detection label and a thermocouple on the upper floor slab 121 of the manhole 10, exposes them for a predetermined period, and measures the temperature of the thermocouple and the internal temperature and humidity of the manhole 10 while checking whether the submergence detection label exhibits a change of color, to evaluate the condensation occurrence condition. However, as compared to the experiment performed using the actually provided manhole 10, the simulation has an advantage that evaluation results can be obtained with general versatility because of less bias in the evaluation results due to the environment of the manhole 10.

In the present embodiment, in step S21, the worker measures only the internal temperature of the manhole 10. In step S21, the worker may also measure the internal temperature of the manhole 10 and the internal humidity of the manhole 10 in addition to the internal temperature of the manhole 10. In this manner, the internal dew point temperature of the manhole 10 can be derived, and therefore the prediction accuracy of the degradation predicting method according to the present embodiment can be improved.

In the present embodiment, the worker uses manholes 10 provided throughout Japan to determine the threshold of underground depth at which the manholes 10 throughout Japan are less prone to degradation. In an embodiment of the present invention, the worker may also use manholes 10 provided in respective regions in different climate divisions to determine the threshold of underground depth at which the manholes 10 in the respective regions are less prone to degradation. The number of manholes 10, the regions where the manholes 10 are provided, and the like are not particularly limited.

While the above-described embodiment has been described as a representative example, it is apparent to a person skilled in the art that a number of changes and replacements can be made within the spirit and scope of the present invention. Thus, the above-described embodiment should not be construed as limiting the present invention, and various modifications and changes are possible without departing from the scope of the claims. For example, the order of the processes shown in the flowcharts in the embodiment can be changed as appropriate without limitation to the above description. It is also possible to combine a plurality of processes into one process or divide one process.

REFERENCE SIGNS LIST 10 manhole (reinforced concrete structure buried in the ground)
20 acrylic test piece
30 constant temperature and humidity chamber
40 pipeline
50 corrosion sensor
51 substrate
52 insulating paste
53 conductive paste
70 reinforcing steel
110 neck portion
120 housing
121 upper floor slab
122 lower floor slab
123 side wall portion 130 steel lid
140 pipeline

The invention claimed is:

1. A degradation predicting method for predicting degradation of a reinforced concrete structure buried in the ground, the method comprising:
- a condensation occurrence condition evaluating step of evaluating a condensation occurrence condition on which condensation occurs on reinforcing steel;
- a condensation time calculating step of calculating a condensation time that is a total time in which condensation occurs on the reinforcing steel based on the condensation occurrence condition for each of a plurality of the reinforced concrete structures;
- a threshold determining step of determining a threshold of underground depth at which the reinforced concrete structure is less prone to degradation based on a relationship between the condensation time and a underground depth of the reinforced concrete structure; and
- a degradation predicting step of predicting degradation of a prediction-target reinforced concrete structure based on the threshold.

2. The degradation predicting method according to claim 1, wherein the condensation time calculating step comprises:
- a step of measuring a temperature of the reinforcing steel and an internal temperature of the reinforced concrete structure for each of the plurality of the reinforced concrete structures; and
- a step of calculating the condensation time based on the condensation occurrence condition and a temperature difference between the temperature of the reinforcing steel and the internal temperature of the reinforced concrete structure.

3. The degradation predicting method according to claim 1, wherein the condensation occurrence condition is that a temperature difference between a temperature of the reinforcing steel and an internal temperature of the reinforced concrete structure is $1.0°$ C. or more.

4. The degradation predicting method according to claim 1, wherein the condensation occurrence condition is evaluated by using a constant temperature and humidity chamber that simulates the reinforced concrete structure and in which an acrylic test piece is provided, and based on a corrosion current of a corrosion sensor stuck on the acrylic test piece and a temperature difference between a temperature of the corrosion sensor and an internal dew point temperature of the constant temperature and humidity chamber.

* * * * *